(12) United States Patent
Price et al.

(10) Patent No.: US 10,571,409 B2
(45) Date of Patent: Feb. 25, 2020

(54) X-RAY APPARATUS

(71) Applicant: NIKON METROLOGY NV, Leuven (BE)

(72) Inventors: Ben Price, Tring (GB); Michael Beechey, Chesham (GB); James Smith, Ivinghoe (GB)

(73) Assignee: NIKON METROLOGY NV, Leuven (BE)

( * ) Notice: Subject to any disclaimer, the term of this patent is extended or adjusted under 35 U.S.C. 154(b) by 0 days.

(21) Appl. No.: 16/220,626

(22) Filed: Dec. 14, 2018

(65) Prior Publication Data

US 2019/0137417 A1     May 9, 2019

Related U.S. Application Data

(62) Division of application No. 15/503,318, filed as application No. PCT/EP2015/068555 on Aug. 12, 2015.

(30) Foreign Application Priority Data

Aug. 13, 2014    (GB) .................................. 1414395.2

(51) Int. Cl.
    *G01N 23/02*      (2006.01)
    *G01N 23/20025*   (2018.01)
    *G01N 23/2204*    (2018.01)

(52) U.S. Cl.
    CPC ....... *G01N 23/02* (2013.01); *G01N 23/20025* (2013.01); *G01N 23/2204* (2013.01);
(Continued)

(58) Field of Classification Search
None
See application file for complete search history.

(56) References Cited

U.S. PATENT DOCUMENTS

| | | |
|---|---|---|
| 5,344,238 A | 9/1994 | Roch |
| 5,627,874 A | 5/1997 | Smallbone |

(Continued)

FOREIGN PATENT DOCUMENTS

| | | |
|---|---|---|
| DE | 1217100 B | 5/1966 |
| DE | 102011005732 A1 | 9/2012 |

(Continued)

OTHER PUBLICATIONS

International Search Report and Written Opinion in related International Application No. PCT/EP2015/068555 dated Jan. 19, 2016, 16 pages.

(Continued)

*Primary Examiner* — Hoon K Song
(74) *Attorney, Agent, or Firm* — Andrew M. Calderon; Roberts Mlotkowski Safran Cole & Calderon, P.C.

(57) ABSTRACT

An equipment mount for an x-ray apparatus is disclosed. The mount includes a main shield element, a peripheral shield element and a secondary shield element arranged to permit a mounting element to pass through the main shield element in a shielded manner. A support apparatus for an x-ray apparatus is also disclosed. The support apparatus comprises a separable bearing for translating a support part between a first position and a second position and an elevator mechanism for translating the support part from the second position to a third position, thereby separating the bearing.

17 Claims, 3 Drawing Sheets

(52) U.S. Cl.
CPC . *G01N 2223/308* (2013.01); *G01N 2223/309* (2013.01); *G01N 2223/419* (2013.01)

(56) References Cited

U.S. PATENT DOCUMENTS

| | | |
|---|---|---|
| 2006/0133580 A1 | 6/2006 | Vezina |
| 2007/0223657 A1 | 9/2007 | Birdwell |
| 2009/0116614 A1 | 5/2009 | Kotowski et al. |
| 2009/0141862 A1 | 6/2009 | Dunham et al. |
| 2009/0285360 A1 | 11/2009 | Cao et al. |
| 2012/0198625 A1 | 8/2012 | Jackson |
| 2013/0115499 A1* | 5/2013 | Joye .................. H01M 2/1077 429/99 |
| 2015/0294832 A1 | 10/2015 | Hakoda et al. |

FOREIGN PATENT DOCUMENTS

| | | |
|---|---|---|
| EP | 0314552 | 5/1989 |
| EP | 1837644 A1 | 9/2007 |
| JP | S52-7263 | 1/1977 |
| JP | 05119193 | 5/1993 |
| JP | H05-306972 | 11/1993 |
| JP | 2004-016610 | 1/2004 |
| JP | 2006-214924 | 8/2006 |
| JP | 2008-505340 | 2/2008 |
| JP | 2010073477 | 4/2010 |
| WO | 2006003430 | 1/2006 |
| WO | 2010094719 | 8/2010 |
| WO | 2012123216 | 9/2012 |
| WO | 2014050931 A1 | 4/2014 |

OTHER PUBLICATIONS

Japanese Office Action in related JP Application No. 2017-507729 dated Oct. 22, 2018, 6 pages.
Japanese Office Action in related JP Application No. 2017-507729 dated Jan. 30, 2018, 7 pages.
Search Report in related GB Application No. GB14114395.2 dated Jan. 30, 2015, 4 pages.
Office Action from US. Appl. No. 16/220,632 dated Apr. 11, 2019. 7 pages.
Notice of Allowance from U.S. Appl. No. 15/503,318 dated Apr. 1, 2019; 7 pages.
Japanese Office Action in related JP Application No. 2018-098659 dated Mar. 11, 2019, 11 pages.
Japanese Notice of Allowance in related JP Application No. 2017-507729 dated Jun. 10, 2019, 6 pages.
Notice of Allowance issued in related U.S. Appl. No. 16/220,632 dated Oct. 24, 2019, 5 pages.

* cited by examiner

X-RAY APPARATUS

FIELD

The present disclosure relates to an x-ray apparatus, and also to an equipment mount, a support structure and a manipulator stage for use in such an x-ray apparatus.

TECHNICAL BACKGROUND

X-ray imaging systems, especially x-ray imaging systems for use in industrial or scientific applications, typically use an enclosed configuration, in which the x-ray source and the x-ray detector are arranged in an x-ray shielded enclosure having appropriate apertures, usually termed windows, for introducing and removing the sample under investigation. Such a configuration allows the operator to conveniently operate the machine and to make necessary adjustments to the imaging systems and the sample position in relative safety.

Recently, higher-power x-ray systems have enabled the imaging of increasingly heavy and bulky samples. In particular, CT imaging, which can reconstruct a volumetric density map of an object from a series of x-ray projections taken at various angles about an axis defined by the sample under investigation have been proposed for imaging structures as large as engine blocks, for example to determine and analyse the presence of defects.

However, for such applications, the increase in the size of and the weight of the sample under investigation requires the enclosure to be substantially enlarged, not only to accommodate the larger sample but also to allow for increased dimensions of the various components which bear the weight of the sample, to avoid undesirable distortion or breakage.

Scaling up the apparatus to cope with such heavy or bulky loads causes an increase in the footprint of such apparatus and also adds to the cost.

Accordingly, there is a need for an x-ray apparatus which is able to accommodate relatively large samples in a compact form factor.

SUMMARY

According to a first aspect of the present invention, there is provided an equipment mount for an x-ray apparatus, the mount comprising: a main shield element having at least one aperture penetrating the shield element from one side of the shield element to the other side of the shield element; a mounting element arranged to extend through the aperture of the main shield element and having an equipment-supporting surface on the one side of the aperture and having a base surface on the other side of the aperture; a peripheral shield element extending from a region of the main shield element surrounding the aperture to at least partly surround at least part of the mounting element; and a secondary shield element arranged at one of the base surface and the equipment-supporting surface of the mounting element and extending towards the main shield element to at least partly surround an outer periphery of at least part of the peripheral shield element.

In one configuration, the aperture defines an axis normal thereto, and the main shield element, the peripheral shield element and the secondary shield element are together configured and arranged such that x-ray radiation incident at an angle greater than 45 degrees from at least one direction about the axis will impinge on at least one of the plate shield element, secondary shield element and peripheral shield element, preferably 30 degrees, more preferably 15 degrees, most preferably 5 degrees, and preferably from all directions within 45 degrees of the at least one direction, more preferably within 180 degrees of the at least one direction, most preferably within 360 degrees of the at least one direction.

In one configuration, the main shield element is a plate.

In one configuration, the peripheral shield element is substantially a sector of a hollow cylinder or hollow cone, preferably substantially an entire hollow cylinder or cone.

In one configuration, the secondary shield element comprises a secondary shield plate and a peripheral secondary shield wall extending from the secondary shield plate toward the main shield element.

In one configuration, the peripheral secondary shield wall is substantially a sector of a hollow cylinder or hollow cone, preferably substantially an entire hollow cylinder or cone.

In one configuration, the mounting element comprises a rod portion extending between the equipment-supporting surface and the base surface.

In one configuration, the main shield element, peripheral shield element and secondary shield element are provided on one of the one side of the aperture or the other side of the aperture, and a further main shield element, further peripheral shield element and further secondary shield element are provided on the other of the one side of the aperture or the other side of the aperture.

In one configuration, the further main shield element, further peripheral shield element and further secondary shield element are respectively configured as the main shield element, peripheral shield element and secondary shield element.

In one configuration, the secondary shield element has an aperture and the mounting element extends through the aperture of the secondary shield element.

In one configuration, the secondary shield element has an aperture and the equipment-supporting surface of the mounting element is arranged at the main-shield element side of the aperture of the secondary shield element.

According to a second aspect of the present invention, there is provided a support apparatus for an x-ray apparatus, the enclosure comprising: a base part; a support part for supporting a component of the x-ray apparatus; a bearing having a first bearing element provided to the base part and a second bearing element provided to the support part for allowing the support part to be translated relative to the base part from a first position to a second position with the first bearing element in contact with the second bearing element; an elevator provided to the base part and arranged to translate the support part from the second position to a third position, thereby to relatively separate the first bearing element and the second bearing element.

In one configuration, the bearing is a slide bearing and the first and second bearing elements are flat bearing surfaces arranged parallel and mutually approximate.

In one configuration, the bearing is a roller bearing, the first bearing element is one of a roller and a bearing surface against which the roller is arranged to roll and the second bearing element is the other of the roller and the bearing surface.

In one configuration, a vibration reduction element is provided to inhibit the transmission of vibrations between the sample support part and the base part when the sample support part is in the third position.

In one configuration, the vibration reduction element is provided between the elevator and the support part.

In one configuration, wherein the vibration reduction element is provided between the elevator and the base part.

In one configuration, the vibration reduction element is provided as the elevator.

In one configuration, the vibration reduction element comprises a pneumatic piston.

In one configuration, a guard is provided to the first bearing element to prevent separation of the first bearing element and the second bearing element when the sample support part is not in the second position.

In one configuration, the first position is a position relatively nearer an access aperture of an enclosure of the x-ray apparatus than the second position and the third position is a position for x-ray irradiation.

According to a third aspect of the present invention, there is provided a manipulator stage for an x-ray apparatus, the stage comprising: a sample stage for holding a sample undergoing x-ray exposure; a first support structure arranged to support the sample stage at a first position on the first support structure; a second support structure arranged to support the first support structure at a second position on the sample support structure displaced in a horizontal direction from the first position and configured such that that the first support structure may be translated in a vertical direction while remaining supported by the second support structure; a third support structure arranged to support the first support structure at a third position on the sample support structure displaced in a horizontal direction from the first position such that the first position is between the second position and the third position in a horizontal direction, wherein the third support structure comprises a drive mechanism for translating the first support structure in a vertical direction.

In one configuration, the manipulator stage further comprises a reference member to which the second and third support structures are provided and relative to which the first support structure is able to be translated by the drive mechanism.

In one configuration, the sample stage comprises a rotational stage for adjusting the position of the sample relative to the first support structure.

In one configuration, the drive mechanism is a screw drive comprising a translating element and a rotating element, the first support structure being connected to the translating element of the screw drive.

In one configuration, the drive mechanism is a belt drive, the first support structure being connected to the belt of the belt drive.

In one configuration, the second and third positions are at each end, respectively, of the first support structure.

In one configuration, the first position is centrally located between the second and third positions.

In one configuration, the second support structure comprises a track configured to retain a follower arranged to support the third position of the first support structure.

In one configuration, the track comprises a linear groove and the follower comprises a slider retained within the groove or the track comprises a bar and the follower comprises a carriage retained around the bar.

In one configuration, wherein the first support structure is a horizontal beam.

According to a fourth aspect of the present invention, there is provided an x-ray apparatus having an x-ray source, a manipulator stage and an x-ray detector, the x-ray apparatus comprising an equipment mount according to the first aspect arranged to support the manipulator stage.

According to a fourth aspect of the present invention, there is provided an x-ray apparatus having an x-ray source, a manipulator stage and an x-ray detector, the x-ray apparatus having a support structure according to the second aspect arranged to support one of the x-ray source, the manipulator stage and the x-ray detector.

According to a fifth aspect of the present invention, x-ray apparatus having an x-ray source, a manipulator stage and an x-ray detector, the manipulator stage being a manipulator stage according to the third aspect.

BRIEF DESCRIPTION OF THE DRAWINGS

For a better understanding of the present invention, and to show how the same may be carried into effect, reference will be made, by way of example only, to the accompanying drawings, in which.

DETAILED DESCRIPTION

Figure 1:
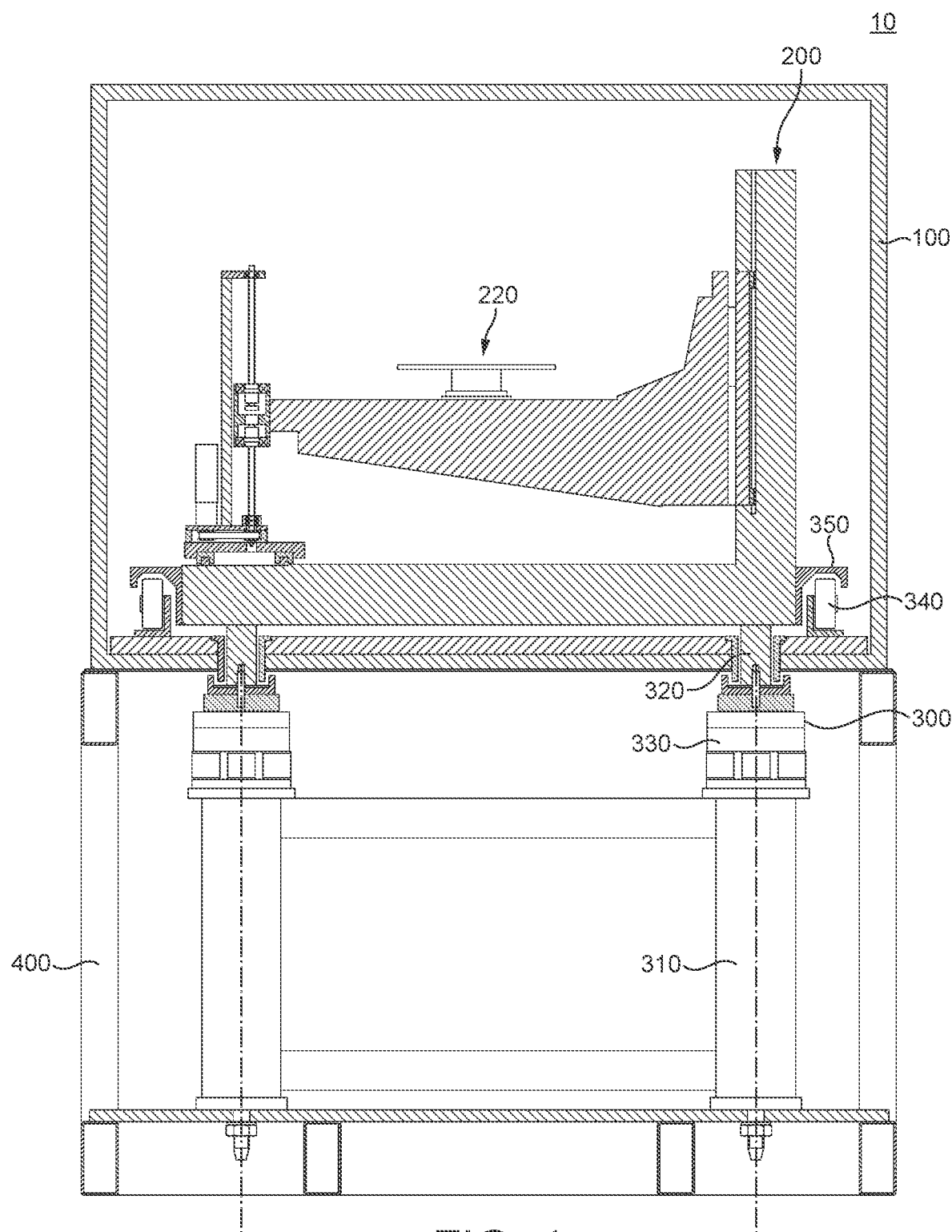
FIG. 1 is a cross-sectional view of an x-ray apparatus in accordance with an embodiment of the present invention.

FIG. 1 shows a transverse cross-section through an x-ray apparatus according to a first embodiment of the present invention.

Not visible in FIG. 1 are an x-ray source and an x-ray detector. However, in the configuration of FIG. 1, an x-ray source can be imagined from the viewer's eye position, and an x-ray detector can be imagined beyond the plane of the paper in a viewing direction of the viewer, with sample stage 220 interposed. Therefore, a sample placed on sample stage 220 will lie between the x-ray source and the x-ray detector, and x-ray imaging can be performed on the sample. If the detector is an imaging array, a projected image of the sample may be obtained, and if the sample is rotated on sample stage 220 and projections taken at a variety of angular orientations, CT imaging techniques may be used to reconstruct a volumetric density map of the object, allowing investigation of the internal structure.

In the below disclosure, the z-direction will be taken to be an axis along the beam path, into the page; the y-direction, or gravity direction, will be taken to be an axis vertical in the page and perpendicular to the z-direction, and the x-direction will be taken to be an axis crossing the page horizontally, perpendicular to the z-direction and y-direction.

The arrangement of FIG. 1 can allow a relatively heavy sample to be analysed, in a relatively compact configuration.

A first aspect of the embodiment of FIG. 1 which permits such a relatively compact configuration is the provision of equipment mounting elements 320 which penetrate the shielded enclosure 100 enclosing the sample stage, the x-ray detector and the x-ray source, allowing the sample to be supported by a relatively robust support frame 310 without requiring an increase in the size of the shielded enclosure 100 and also without permitting undesired leakage of x-ray radiation to an outside of the enclosure.

Figure 2:
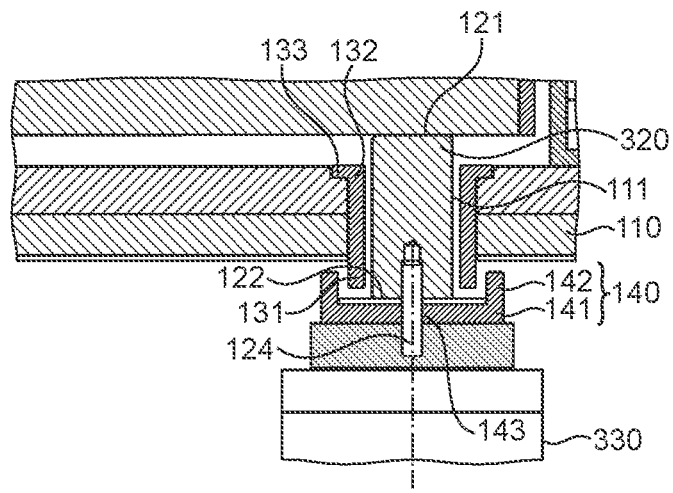
FIG. 2 is an enlarged detail of FIG. 1 showing a mounting element and accompanying shielding elements.

The configuration of shielded enclosure 100 which may contribute to the compact size of the x-ray apparatus is showing in detail in FIG. 2. In FIG. 2, the shielded enclosure is provided with a main shield element 110, which here takes the form of a base plate of the enclosure. An aperture 110 passes through the main shield element from an inside to an outside, allowing a mounting element 320 to pass therethrough.

The mounting element 320 is formed as a rod, and has at an inside end an equipment supporting surface 121 and at an outside end a base surface 122. Mounting element 320 bears the weight of any elements which rest or attached to the equipment supporting surface 121 and transfers the weight to anti-vibration mount 330, which is located outside the enclosure. Locating the anti-vibration mount 330 outside the enclosure permits the enclosure to be more compact than if the enclosure were required to enclose the entire apparatus, including the anti-vibration mount 330 together with the anti-vibration mount support frame 310 also visible in FIG. 1.

However, providing an aperture 111 in a wall of a shielded enclosure such as main shield element 110 would normally permit undesired leakage of x-ray radiation to the exterior of the enclosure. Accordingly, the present embodiment employs additional shielding elements to inhibit the undesired leakage of x-ray radiation.

Specifically, extending from a region of the main shield element surrounding the aperture so as to at least surround part of the length of mounting element 320 protruding beyond a lower plane of the main shield element 110 is a peripheral shield element. Further, provided at the base surface 122 of the mounting element 320 is a secondary shield element 140, which here is formed as a secondary shield plate 141 extending in a plane normal to an axis traversing aperture 111 to beyond an outer circumference of peripheral shield element 131 and having a secondary shield wall 142 extending therefrom so as to surround at least a part of peripheral shield element 131.

By means of such a configuration, x-rays impinging on aperture 111 are prevented from exiting to the outside of the apparatus by the presence of the peripheral shield element 131 and the secondary shield element 140.

If secondary shield element 140 overlies and covers the entire area of aperture 111, such a configuration will completely inhibit the transmission of x-rays, provided an adequate thickness of x-ray absorbing material is used in the construction of the peripheral shield elements and secondary shield element. However, to allow a secure coupling between mounting element 320 and anti-vibration mount 330, it may be advantageous to provide a threaded bore 143 in base surface 122 of mounting element 320 to accept a coupling bolt 124. To achieve this, coupling bolt 124 passes through an aperture 143 formed in secondary shield plate 141.

In such a configuration, x-rays travelling down the axis of bore 123 will not impinge upon secondary shield plate 141, but will instead pass through aperture 143. If there is concern about such x-rays, a radiodense material can be used as coupling bolt 124 to adequately inhibit the passage of x-rays through aperture 143, or otherwise it may be accepted that x-rays arriving at a small range of angles on the axis of bore 123 will not be absorbed, and the x-ray source will be positioned inside enclosure 100 so as to avoid generating x-rays travelling at such angles.

If the base surface bore 123 and the aperture 111 in the main shield element 110 share an axis, it may be allowed for x-rays travelling at an angle of 5 degrees, 10 degrees, 15 degrees, 25 degrees or 30 degrees to this axis to be permitted to exit the enclosure, and the dimensions of the peripheral shield element 131 and secondary shield element 140 can be appropriately chosen.

Although FIG. 2 shows the peripheral shield element 131 and the secondary shield element 140 provided outside the enclosure, similar elements may be provided inside the enclosure additionally to, or as an alternative to, the configuration of FIG. 2, in which they are provided outside the enclosure. Such configurations can provide even greater shielding against x-rays travelling at angles close to the axis of aperture 111 and/or base surface bore 123.

Furthermore, the configuration of FIG. 2 shows the mounting element 320 as being vertically oriented, so as to bear the direct weight of equipment resting on the equipment supporting surface 121. However, without limitation, aperture 111 may be formed in any suitable surface, including floor, walls or ceiling of enclosure 100, so as to allow equipment to be suspended from the ceiling or walls. In such configurations, the equipment supporting surface 121 may additionally be provided with a bore for accepting a coupling bolt, or with another suitable fixing means, such as a hook or bracket, for attaching the equipment to be suspended.

A variety of modifications of the configuration of FIG. 2 may be considered. For example, if it is certain that x-rays will be generated only from one direction, the shield elements may be arranged only to protect against x-rays travelling from that direction. In such a configuration, it may be sufficient to provide peripheral shield element 131 to only partially surround mounting element 320 at the side opposite to which it is expected that x-rays are to be generated. For example, the peripheral shield element can be provided as a half-cylinder. Furthermore, it may be sufficient only to provide a secondary shield element 140 on the side of aperture 111 opposite to the direction from which x-rays are expected to be generated. Of course, if peripheral shield element 131 and secondary shield element 140 are provided inside enclosure 100, it will be necessary for them to be provided on the side of aperture 111 from which x-rays are intended to impinge, rather than on the opposite side thereto.

Furthermore, although peripheral shield element 131 has been shown in generally cylindrical form and the secondary shield element has been shown as having a plate portion 141 and a cylindrical wall 142, variations on these configurations are possible. For example, peripheral shield element 131 and secondary shield wall 142 may extend as a portion of a hollow cone projecting inwardly or outwardly from aperture 111, and the secondary shield element 140 may be formed, for example, as a hemispherical cup. The configuration shown in FIG. 2 is presently preferred from the point of view of making efficient use of space.

In the configuration of FIG. 2, on a side of main shield element 110 opposite to peripheral shield element 131 and secondary shield element 140, an inwardly projecting internal shield element 132 is shown, having generally cylindrical form and with an internal flange 133 projecting outwardly from an inner end of shield element 132. While it is not essential to provide such a configuration, the provision of such additional shielding elements can improve the overall shielding, and can permit the peripheral shield element 131, and the secondary shield 140 to be made thinner.

While FIG. 2 shows mounting element 320 passing through aperture 111, a similar configuration of main shield element 110, aperture 111, peripheral shield element 131 and secondary shield element 140 can be used to screen any aperture traversing the wall of the enclosure, including apertures for the provision of services such as electrical power and cooling water, as well as control electronics and signals passed on optical fibres. However, in the configuration of FIG. 1, a principal advantage of such a configuration is that it permits the bulky support elements such as the anti-vibration mount 330, and the anti-vibration mount support frame 310 to be positioned outside of the shielded enclosure 100, thereby keeping the size and weight of the shielded enclosure to a relatively more compact form.

As a second aspect of the embodiment of FIG. 1 which permits such a relatively compact configuration, the configuration shown in FIG. 1 also includes elements which enable the samples to be easily withdrawn from the enclosure.

In conventional x-ray apparatuses, it is normal to provide a window or other closable aperture in the enclosure to allow the operator to insert and remove samples. However, as the samples become larger and heavier, it becomes relatively more difficult for the operator to insert and remove the samples unaided. In some cases, special handling equipment such as cranes or trolleys must be used to transport the samples, and it is then generally difficult for the operator to transfer the sample into the enclosure. Providing windows which are large enough for even large or heavy samples to be easily introduced and removed from the enclosure tends to increase the overall size of the shielded enclosure 100. Accordingly, the embodiment of FIG. 1 has features which allow the sample stage 220 to be withdrawn from the enclosure, or at least moved closer to a loading position or loading aperture, to allow samples to more conveniently introduced and withdrawn.

Figure 3:
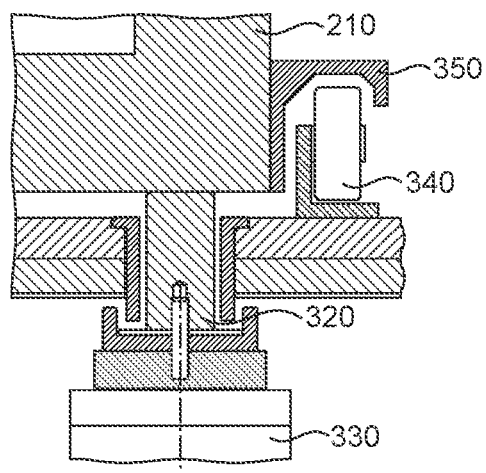
FIG. 3 shows a detail of FIG. 1 depicting aspects of the enclosure of the x-ray apparatus.

Particular elements of the system which permit such easier loading are shown in FIG. 3. With reference to FIG. 1, sample stage 220 forms part of manipulator stage 200 which, as will be discussed later, enables the sample to be easily rotated and translated inside the enclosure. The manipulator stage 200 has as its base reference plate 210, which supports the remaining components of the manipulator stage and defines a reference surface with respect to which the sample is rotated or translated.

As shown in FIG. 3, and as described above, reference plate 210, during operation, rests on mounting elements 320, which are supported by anti-vibration mounts 330. Here, the anti-vibration mount 330 is an active anti-vibration mount which supports the weight of the manipulator stage 200 together with the sample on, for example, a stabilised air column confined within a piston of the anti-vibration mount 330. Manipulator stage 200 is thus appropriately located at an irradiation position, such that the sample is located in an -x-ray beam path.

However, in the present configuration, reference plate 210 is also provided with rail 350, which overhangs a set of rollers 340 which extend in a line out of the plane of the paper, of which one is shown in cross-section in FIG. 3. A corresponding rail is provided on the opposite side of reference plate 210. By this configuration, when the anti-vibration mount 330 is depowered, air is able to be withdrawn from the piston such that the mounting element 320 becomes relatively lower. When the mounting element 320 descends sufficiently far, rail 350 will rest on rollers 340 to form a linear bearing, enabling the manipulator stage 200 to be translated out of the plane of the paper toward the viewer on the rollers. This enables the manipulator stage to be translated to a loading position, for example beneath a crane access hatch in the sealing of the enclosure or otherwise entirely out of the enclosure via a window, door or aperture in the wall of the enclosure, to enable the sample to be easily loaded or withdrawn.

Once appropriate operations have been performed on the sample, the reverse operation is then possible, in which the manipulator stage 200 is translated along the linear bearing formed by rail 350 and roller 340 from the loading position to the irradiation position, activation of the anti-vibration mounts 330 then serves to elevate the manipulator stage 200 such that rail 350 becomes spaced from roller 340 and the manipulator stage 200 is fully supported via mounting element 320 on anti-vibration mount 330.

For increased security, although not shown in FIG. 3, recesses may be formed in the base of reference plate 210 to accept mounting elements 320, to prevent inadvertent translation of reference plate 210 when supported in the irradiation position.

Of course, a variety of modifications of FIG. 3 may be contemplated, including situations having no anti-vibration mount, but rather simply a hydraulic or mechanised lift to elevate mounting elements 320 into contact with the base of reference plate 210 to lift rail 350 clear of rollers 340. Further, the anti-vibration mount can provided as a passive damper, such as a resilient support, positioned between mounting element 320 and reference plate 210, between mounting element 320 and the elevator mechanism, or between the elevator mechanism and a support frame for the elevator mechanism.

Furthermore, alternatives to the above-disclosed configuration of rollers 340 and rails 350 may be contemplated, including arrangements in which the rollers are provided to the manipulator stage and the rails are provided to the base of the enclosure, or configurations in which other linear bearings are substituted, such as sliding bearings or even non-contact air or magnetic bearings. Furthermore, such a configuration can be used even with conventional enclosures in which the anti-vibration mounts and even the anti-vibration frame are enclosed within the enclosure, without limitation.

Finally, such a configuration can be used to support other heavy or bulky elements of the x-ray apparatus, such as the gun or the detector, so that they can easily be removed to an access region of the enclosure, or even to an outside of the enclosure, for maintenance or adjustment.

As a second aspect of the embodiment of FIG. 1 which permits such a relatively compact configuration, the embodiment has a manipulator stage adapted for the supporting of heavy or bulky samples.

Figure 4:
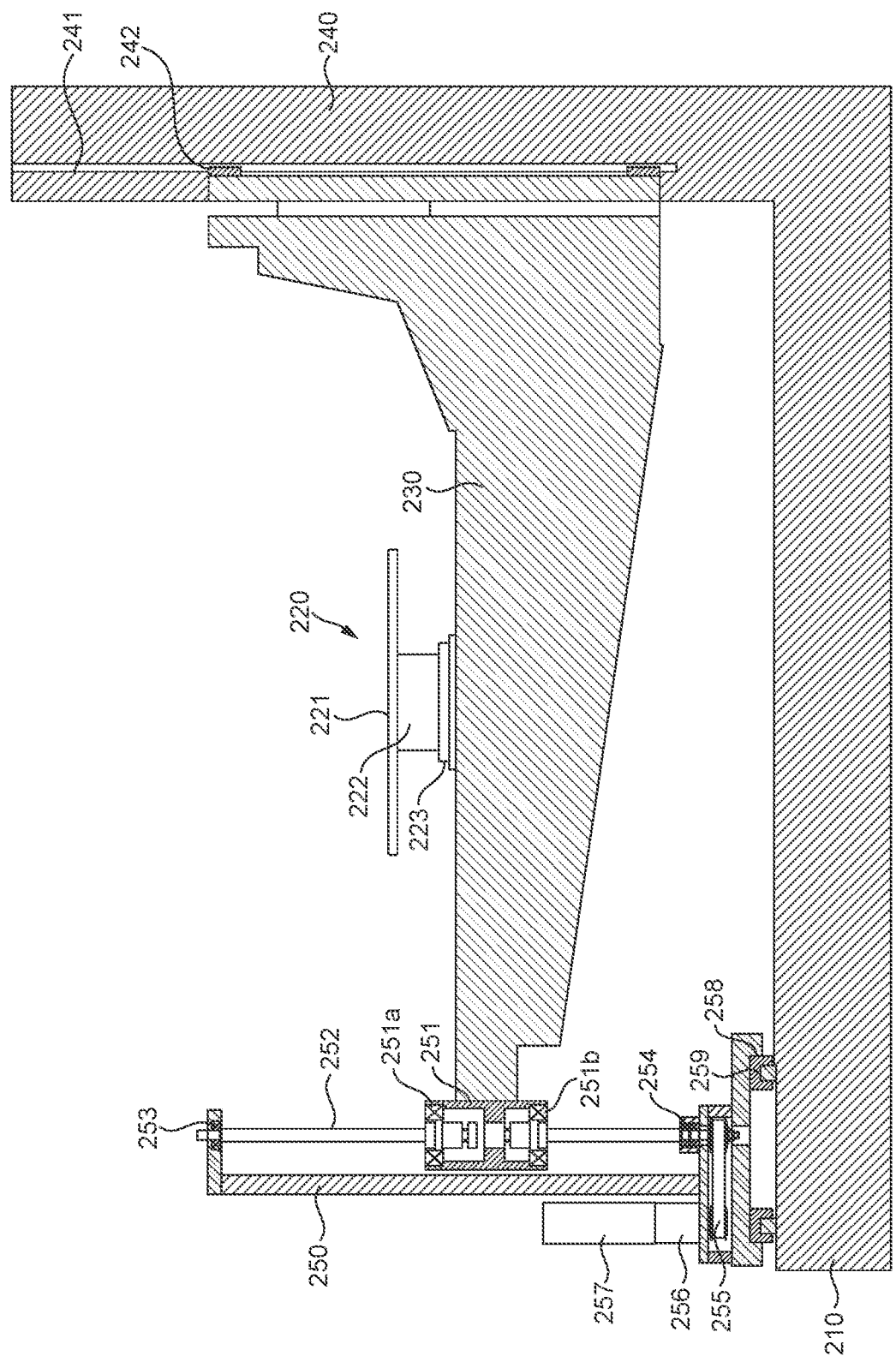
FIG. 4 shows a detail of FIG. 1 depicting a manipulator stage being an embodiment of the present invention.

Particularly, as shown in FIG. 4, manipulator stage 200 has a first support member 230 which supports, at a position along its length, sample stage 220. Sample stage 220 includes platform 221, which provides a sufficiently large, flat surface so as to support the sample. Platform 221 is supported in turn by rotary drive 222 and x-translation carriage 223. Rotary drive 222 enables controlled rotation of platform 221 about an axis aligned with the y-direction, while x-translation carriage 223 allows translation of rotary drive 222 together with platform 221 in the x-direction along a first support member 230. Sample stage 220 is thus supported at an approximately central position of the first support member 230.

By using the x-translation carriage 223 of sample stage 220, the position of the sample in the cross-beam direction can be adjusted, while by rotating the sample using rotary drive 222, projection x-ray images can be obtained at various angles passing through the sample to enable a volumetric density map to be generated through the CT process.

In the present embodiment, first support member 230 takes the form of a beam, supported at one end by a vertical second support member 240 and at the other end by a vertical third support member 250. The beam is here shown to be reinforced by a reinforcement portion which is thicker at the one end than the other end, although beam configurations which have an arch form or beam configurations which have an uniform cross section are also usable.

Second support member 240 provides a groove 241 in which a follower 242 rides, such that the first support member can be raised and lowered in the y-direction with the follower 242 sliding within groove 241. This configuration passively supports the one end of the first support member while allowing free y-direction movement. Equivalently, other constructions which permit the first support member to be raised and lowered while being securely supported may be used, including a configuration having a carriage which rides along the outside of second support member 240, the carriage having inner bearing surfaces which cooperate with outer bearing surfaces of the second support member to enable such free translation to take place.

In contrast, third support member 250 supports the other end of first support member 230 in an active manner, wherein a drive mechanism is provided to adjust the height of the first support member in the y-direction relative to reference plate 210. To achieve such active drive, the third support member 250 includes ball screw 252 and follower nut 251, which is connected to the other end of the first support member 230 not supported by the second support member. Ball screw 252 is supported by radial bearing 253 at the top and fixed angular contact bearing 254 at the bottom, and is driven via drive belt 255 and gear box 256 by stepper motor 257. In such a configuration, the fixed angular contact bearing 254 removes any end float or play, and takes most of the axial thrust during operation. In contrast, radial bearing 253 allows the upper end of ball screw 252 to float, in order to compensate for expansion and minor misalignment of the drive, while reducing any bending moment on the ball screw 252.

Accordingly, by such a configuration, the vertical position of the first support member 230 may be conveniently adjusted by driving ball screw 252 to raise or lower one end of the first support member while allowing the other end of the first support member 230 to follow the movement.

To allow translation of the sample stage 220 in the z-direction, namely along the x-ray beam line in order to permit the magnification to be adjusted, the third support member 250 is supported on a z-carriage 258 which runs on z-rails 259 mounted to reference plate 210. Although not shown in FIG. 4, the first support member 230 is also supported at the second-support-member side by a second follower riding in a second groove formed on the first follower to allow the first support member to translate as a whole in the z-direction in a free manner, without twisting. Thus, by means of the cooperating rotary drive 222, x-translation carriage 223, y-adjustment ball screw 252 and z-carriage 258, sample stage 220 may be translated in each of the x-, y- and z-directions while also being rotated about an axis parallel to the y-axis.

By supporting first support member 230 at both ends with respect to the x-direction, placing even a bulky or heavy load on sample stage 220 will not cause the first support member 230 to distort and the sample stage 220 to become inclined to the x-z plane. Thus, even heavy or bulky samples may be imaged without inaccuracy.

Of course, a variety of modifications are possible to the configuration shown in FIG. 4, including the use of a belt drive, rather than a ball screw and nut, to support and adjust the position of the third-support-member end of the first support member 230, and the possibility of providing active drive means, such as the cooperating ball screw 252 and nut 251, to each end of the first support member.

In the configuration shown in FIG. 4, nut 251 is configured as two ball screw nuts mounted back-to-back so that the forces generated between the ball screw 252 and the nut 251 are transferred to the support member 230 via the radial bearings 251a and 252b of each respective nut. The z-carriage assembly may also be driven by a belt structure or a ball screw in a similar manner to the third support member 250, or may be directly driven by means of a rack and pinion drive. For example, a driven pinion could be mounted on the z-carriage 258 to engage with a rack lying between z-rails 259 to allow the z-carriage to be driven in the z-direction.

Although second support member 240 and third support member 250 are, in the present embodiment, supported by reference plate 210, reference plate 210 is provided mainly for stability and structural strength. As an alternative, each of the second support member 240 and third support member 250 could be directly supported on, for example, mounting elements 320, shown in FIG. 1, especially if z-direction adjustment was not required.

It is expected that one skilled in the art will be able to modify and adapt the above disclosure to suit his own circumstances and requirements within the scope of the present invention, while retaining some or all technical effects of the same, either disclosed or derivable from the above, in the light of his common general knowledge of the art. All such equivalents, modifications or adaptions fall within the scope of the invention hereby defined and claimed.

The invention claimed is:

1. An equipment mount for an x-ray apparatus, the mount comprising:
   a main x-ray shield element having at least one aperture penetrating the main x-ray shield element from one side of the main x-ray shield element to the other side of the main x-ray shield element;
   a mounting element arranged to extend through the aperture of the main x-ray shield element and having an equipment-supporting surface on the one side of the aperture and having a base surface on the other side of the aperture;
   a peripheral x-ray shield element extending from a region of the main x-ray shield element surrounding the aperture to at least partly surround at least part of the mounting element; and
   a secondary x-ray shield element arranged at one of the base surface and the equipment-supporting surface of the mounting element and extending towards the main x-ray shield element to at least partly surround an outer periphery of at least part of the peripheral x-ray shield element.

2. An equipment mount for an x-ray apparatus, the mount comprising:
   a main shield element having at least one aperture penetrating the shield element from one side of the shield element to the other side of the shield element;
   a mounting element arranged to extend through the aperture of the main shield element and having an equipment-supporting surface on the one side of the aperture and having a base surface on the other side of the aperture;
   a peripheral shield element extending from a region of the main shield element surrounding the aperture to at least partly surround at least part of the mounting element; and
   a secondary shield element arranged at one of the base surface and the equipment-supporting surface of the mounting element and extending towards the main shield element to at least partly surround an outer periphery of at least part of the peripheral shield element, wherein the aperture defines an axis normal thereto, and the main shield element, the peripheral shield element and the secondary shield element are together configured and arranged such that x-ray radiation incident at an angle greater than 45 degrees from at least one direction about the axis will impinge on at least one of the plate shield element, secondary shield element and peripheral shield element, preferably 30 degrees, more preferably 15 degrees, most preferably 5 degrees, and preferably from all directions within 45 degrees of the at least one direction, more preferably within 180 degrees of the at least one direction, most preferably within 360 degrees of the at least one direction.

3. The equipment mount according to claim 1, wherein the main x-ray shield element is a plate.

4. The equipment mount according to claim 1, wherein the peripheral x-ray shield element is substantially a sector of a hollow cylinder or hollow cone, preferably substantially an entire hollow cylinder or cone.

5. The equipment mount according to claim 1, wherein the secondary x-ray shield element comprises a secondary x-ray shield plate and a peripheral secondary x-ray shield wall extending from the secondary x-ray shield plate toward the main x-ray shield element.

6. The equipment mount according to claim 5, wherein the peripheral secondary x-ray shield wall is substantially a sector of a hollow cylinder or hollow cone, preferably substantially an entire hollow cylinder or cone.

7. The equipment mount according to claim 1, wherein the mounting element comprises a rod portion extending between the equipment-supporting surface and the base surface.

8. The equipment mount according to claim 1, wherein the main x-ray shield element, peripheral x-ray shield element and secondary x-ray shield element are provided on one of the one side of the aperture or the other side of the aperture, and a further main x-ray shield element, further peripheral x-ray shield element and further secondary x-ray shield element are provided on the other of the one side of the aperture or the other side of the aperture.

9. The equipment mount according to claim 8, wherein the further main x-ray shield element, further peripheral x-ray shield element and further secondary x-ray shield element are respectively configured as the main x-ray shield element, peripheral x-ray shield element and secondary x-ray shield element.

10. The equipment mount according to claim 1, wherein the secondary x-ray shield element has an aperture and the mounting element extends through the aperture of the secondary x-ray shield element.

11. The equipment mount according to claim 1, wherein the secondary x-ray shield element has an aperture and the equipment-supporting surface of the mounting element is arranged at the main-x-ray-shield element side of the aperture of the secondary x-ray shield element.

12. An x-ray apparatus having an x-ray source, a manipulator stage and an x-ray detector, the x-ray apparatus comprising an equipment mount arranged to support the manipulator stage, the equipment mount comprising:
 a main shield element having at least one aperture penetrating the shield element from one side of the shield element to the other side of the shield element;
 a mounting element arranged to extend through the aperture of the main shield element and having an equipment-supporting surface on the one side of the aperture and having a base surface on the other side of the aperture;
 a peripheral shield element extending from a region of the main shield element surrounding the aperture to at least partly surround at least part of the mounting element; and
 a secondary shield element arranged at one of the base surface and the equipment-supporting surface of the mounting element and extending towards the main shield element to at least partly surround an outer periphery of at least part of the peripheral shield element.

13. The equipment mount according to claim 1, wherein the main x-ray shield element, the peripheral x-ray shield element, and the secondary x-ray shield element are configured to inhibit leakage of x-ray radiation from the x-ray apparatus.

14. The equipment mount according to claim 1, wherein the mounting element is vertically oriented.

15. The equipment mount according to claim 14, wherein the equipment-supporting surface comprises a bore that accepts a coupling bolt that attaches equipment to be suspended.

16. The equipment mount according to claim 14, wherein the equipment-supporting surface comprises a hook that attaches equipment to be suspended.

17. The equipment mount according to claim 14, wherein the equipment-supporting surface comprises a bracket that attaches equipment to be suspended.

* * * * *